United States Patent
Roessl

(10) Patent No.: US 11,020,070 B2
(45) Date of Patent: Jun. 1, 2021

(54) SPECTRAL MATERIAL DECOMPOSITION FOR PHOTON-COUNTING APPLICATIONS

(71) Applicant: KONINKLIJKE PHILIPS N.V., Eindhoven (NL)

(72) Inventor: Ewald Roessl, Henstedt-Ulzburg (DE)

(73) Assignee: KONINKLIJKE PHILIPS N.V., Eindhoven (NL)

(\*) Notice: Subject to any disclaimer, the term of this patent is extended or adjusted under 35 U.S.C. 154(b) by 710 days.

(21) Appl. No.: 15/317,143

(22) PCT Filed: Jun. 25, 2015

(86) PCT No.: PCT/EP2015/064447
§ 371 (c)(1),
(2) Date: Dec. 8, 2016

(87) PCT Pub. No.: WO2015/197786
PCT Pub. Date: Dec. 30, 2015

(65) Prior Publication Data
US 2017/0100085 A1    Apr. 13, 2017

(30) Foreign Application Priority Data
Jun. 27, 2014   (EP) .................................... 14174799

(51) Int. Cl.
*A61B 6/00* (2006.01)
*G01T 1/17* (2006.01)
*A61B 6/03* (2006.01)

(52) U.S. Cl.
CPC ............ *A61B 6/4241* (2013.01); *A61B 6/032* (2013.01); *A61B 6/482* (2013.01); *A61B 6/5205* (2013.01);
(Continued)

(58) Field of Classification Search
CPC ..... A61B 6/4241; A61B 6/482; A61B 6/5205; A61B 6/032; A61B 6/4233; A61B 6/58; G01T 1/36; G01T 1/17; G01T 7/005
See application file for complete search history.

(56) References Cited

U.S. PATENT DOCUMENTS 6,950,492 B2 \* 9/2005 Besson ................ A61B 6/4035
378/5
7,208,739 B1 \* 4/2007 Yanoff .................... G01T 1/171
250/363.09
(Continued)

FOREIGN PATENT DOCUMENTS

JP    2011055004 A    3/2011
JP    2012029496 A    2/2012
(Continued)

OTHER PUBLICATIONS

Adam S. Wang, "Pulse pileup statistics for energy discriminating photon counting x-ray detectors", Medical Physics, vol. 38, p. 4265-4275. (Year: 2011).\*
(Continued)

*Primary Examiner* — Dani Fox
*Assistant Examiner* — Soorena Kefayati
(74) *Attorney, Agent, or Firm* — Larry Liberchuk

(57) ABSTRACT

A method of processing a signal measured by an energy-resolving detector after passage of radiation through a sample includes receiving a measured count rate for photonic interactions with the detector, fitting a signal model to the detected counts, wherein the signal model is configured to account for a pulse-pile-up effect, the signal model representing a conditional expectation of a frequency of at least uni-directional pulse crossing of at least one energy level, given a physical quantity of a material in the sample,
(Continued)

wherein the signal model is expressed in terms of a Fourier representation of a pulse height variable.

16 Claims, 7 Drawing Sheets

(52) U.S. Cl.
CPC .............. *G01T 1/17* (2013.01); *A61B 6/4233* (2013.01); *A61B 6/58* (2013.01)

(56) References Cited

U.S. PATENT DOCUMENTS

| | | | |
|---|---|---|---|
| 8,055,050 B2 | 11/2011 | Roessl | |
| 9,057,798 B2 | 6/2015 | Seino | |
| 9,508,165 B1* | 11/2016 | Heukensfeldt Jansen | ................... G01T 1/40 |
| 10,281,592 B2* | 5/2019 | Kawata | ................ A61B 6/4241 |
| 2007/0029494 A1 | 2/2007 | Caruba | ..................... G01T 1/17 250/370.11 |
| 2007/0076842 A1* | 4/2007 | Tkaczyk | .............. A61B 6/4042 378/5 |
| 2007/0189443 A1* | 8/2007 | Walter | .................. A61B 6/504 378/4 |
| 2010/0213353 A1* | 8/2010 | Dierickx | ................... G01T 1/17 250/214 R |
| 2010/0215230 A1* | 8/2010 | Bornefalk | ............. G06T 11/005 382/128 |
| 2010/0270472 A1* | 10/2010 | Proksa | .................... G01T 1/171 250/371 |
| 2011/0251828 A1* | 10/2011 | Scoullar | .................. G01T 1/171 702/189 |
| 2013/0146767 A1* | 6/2013 | Seino | ...................... G01T 1/171 250/336.1 |
| 2014/0197307 A1* | 7/2014 | Jorion | .................... G01V 13/00 250/252.1 |
| 2014/0233693 A1* | 8/2014 | Wang | ..................... A61B 6/582 378/5 |
| 2014/0314211 A1* | 10/2014 | Zou | ........................ A61B 6/482 378/207 |
| 2015/0078512 A1* | 3/2015 | Goderer | ................. A61B 6/032 378/19 |
| 2015/0168570 A1* | 6/2015 | Pelc | ........................ G01T 1/247 378/5 |
| 2015/0182176 A1* | 7/2015 | Jin | .......................... G01T 1/171 378/5 |
| 2015/0187052 A1* | 7/2015 | Amroabadi | ........ G01R 33/5611 382/131 |
| 2015/0323687 A1* | 11/2015 | Simpson | ................... G01T 1/36 702/190 |
| 2015/0355114 A1* | 12/2015 | Taguchi | ................. A61B 6/482 378/62 |
| 2016/0370475 A1* | 12/2016 | Kawata | ..................... G01T 1/17 |
| 2017/0023496 A1* | 1/2017 | Persson | ................. G06T 11/005 |

FOREIGN PATENT DOCUMENTS

| | | |
|---|---|---|
| WO | 2008/155679 | 12/2008 |
| WO | 2014002022 | 1/2014 |

OTHER PUBLICATIONS

Katsuyuki Taguchi, "Modeling the performance of a photon counting x-ray detector for CT: Energy response and pulse pileup effects", Medical Physics, vol. 38 No. 2, p. 1089-1102. (Year: 2011).*
Adam S. Wang, "Pulse pileup statistics for energy discrimination photon counting X-ray detectors", Medical Physics, vol. 38, p. 4265-4275. (Year: 2011).*
Katsuyuki Taguchi, "Modeling the performance of photon counting x-ray detector for CT: Energy response and pulse pileup effects", Medical Physics, vol. 38 No. 2, p. 1089-1102 (Year: 2011).*
Hermine Bierme, "A Fourier approach for the level crossings of shot noise processes with jumps", Journal of Applied probability, vol. 49, Edition 1, p. 100-113 (Year: 2012).*
K Taguchi et al in "An analytical model of the effects of pulse pileup on the energy spectrum recorded by energy resolved photon counting x-ray detectors", Med Phys 37(8), Aug. 2010, pp. 3957-3969.
Alvarez, "Energy-selective Reconstructions in X-ray Computerized Tomography", Phys. Med. Biol., 1976, vol. 21, Vo. 5, 733-744.
Schirra et al in "Statistical Reconstruction of Material Decomposed Data in Spectral CT", IEEE Trans on Medical Imaging, vol. 32, No. 7, Jul. 2013.
Biermé, et al., "A Fourier Approach for the Level Crossings of Shot Noise Processes with Jumps", Journal of Applied Probability, 49(1):100-113, 2012.
Schlomka et al., "Experimental feasibility of multi-energy photon-counting K-edge imaging in pre-clinical computed tomography", Phys. Med. Biol. 53 (2008) 4031-4047).
Schirra, et al., "Towards In-vivo K-edge imaging using a new semi-analytical calibration method", Progress in Biomedical Optics and Imaging, SPIE, vol. 9033, 2014.
Roessl, et al., "A Fourier Approach to Model Pulse Pile-Up in Photon-Counting X-ray Detectors", medical physics 43 (3), Mar. 2016.
Wielopolski, "Prediction of the pulse-height spectral distortion caused by the peak pile up effect," Nuclear Instruments and Methods 133, 303-309 (1976).
Gardner, "A generalized method for correcting pulse-height spectra for the peak pile-up effect due to double sum pulses: Part i. predicting spectral distortion for arbitrary pulse shapes," Nuclear Instruments and Methods 140, 289-296 (1977).
Taguchi, "Modeling the performance of a photon counting x-ray detector for CT: Energy response and pulse pileup effects," Med. Phys. 38, 1089-1102 (2011).
Rice, "Mathematical Analysis of Random Noise-Conclusion," Bell Systems Tech. J., vol. 24, p. 46-156 24, 46-156 (1945).
Bierm'e, "Crossings of smooth Shot Noise Processes," 30 p. MAP5 2011-16 MAP5 2011-16, (2011).

* cited by examiner

SPECTRAL MATERIAL DECOMPOSITION FOR PHOTON-COUNTING APPLICATIONS

CROSS REFERENCE TO RELATED APPLICATIONS

This application is the U.S. National Phase application under 35 U.S.C. § 371 of International Application No. PCT/EP2015/064447, filed Jun. 25, 2015, published as WO 2015/197786 on Dec. 30, 2015, which claims the benefit of European Patent Application Number 14174799.8 filed Jun. 27, 2014. These applications are hereby incorporated by reference herein.

FIELD OF THE INVENTION

The invention relates to methods of processing a signal, to related signal processing apparatuses, to computer program elements, and to computer readable media.

BACKGROUND OF THE INVENTION

Computed tomography usually requires X-ray beams with relatively high photon flux. This can hamper the use of energy-sensitive, photon-counting detectors in such imaging systems because the high flux causes pulse pile-up effects that distort the count signals which is turn causes artifacts in images reconstructed from such signals. However, photon counting detectors have proved useful in spectral CT applications where one wishes to achieve material decomposition of the detected signals.

Current trends point to developments of spectral computed tomography scanners that use even higher fluxes and consequently pulse-pile up effects will be rampant which in turn may actually discourage pursing CT applications for material decomposition.

Although, in the present literature, a number of models exist to approximately predict the expected number of counts subject to pulse pile-up, a general, exact solution to the problem is still missing. See for instance K Taguchi et al in "An analytical model of the effects of pulse pileup on the energy spectrum recorded by energy resolved photon counting x-ray detectors", Med Phys 37(8), August 2010, pp 3957-3969. See also Applicant's WO 2008/155679 where a pulse-pile up correction method is described.

SUMMARY OF THE INVENTION

There may therefore exist a need for methods or apparatuses to address the above identified and to better account for pulse-pile-up.

The object of the present invention is solved by the subject matter of the independent claims where further embodiments are incorporated in the dependent claims. It should be noted that the following described aspect of the invention equally apply to the signal processing apparatuses, to the computer program elements and to the computer readable media.

According to a first aspect of the invention there is provided a method of processing a signal measured by an energy-resolving detector system after passage of radiation through a sample, the method comprising:

receiving a measured count rate for photonic interactions with the detector;

fitting a signal model to the detected counts, wherein the model represents the conditional expectation of a frequency of at least uni-directional pulse crossing of at least one energy level (E), given a physical quantity of a material in said sample, wherein the signal model is expressed in terms of a Fourier representation of a pulse height variable (u).

According to one embodiment, the signal model incorporates a Fourier transform of a cumulative spectral response function ($\Phi_R$) of said detector system.

According to one embodiment the Fourier transform is pre-computed.

According to one embodiment the count rate is registered as one or more electronic pulses detected at an instant the one or more pulses having a pulse height and wherein said signal model is based on a description of a random process for the one or more pulses, wherein the random process model is formed from two probability densities, one for the distribution of intervals between two consecutive pulses and the other for the distribution of the pulse height.

According to one embodiment the random process model is that of shot noise.

According to one embodiment, the fitting operation includes solving an objective function based on said model for a parameter for said physical quantity.

According to one embodiment the physical quantity is any one of i) absorption (A), ii) refraction or iii) scatter.

According to one embodiment, a fidelity of the solved for parameters for the physical quantity is independent of a photon fluence of said radiation. By "fidelity" is meant a bias or systematic errors although a mere statistical error (noise) may still differ.

According to one embodiment, the signal model includes a functional description of pulse shape.

According to a second aspect, there is provided a method of processing a signal measured by a photon-counting or energy resolving detector system after passage of radiation through a sample, the method comprising:

receiving a measured count rate for photonic interactions with the detector;

fitting a signal model to the detected counts, wherein the model represents the conditional expectation of a frequency of at least uni-directional pulse crossing of at least one energy level (E), given a physical quantity of a material in said sample, wherein the fitting operation includes solving an objective function for a parameter for said physical quantity, wherein, a fidelity of the solved for parameter for said spectroscopic quantity is independent of a photon fluence of said radiation.

According to one embodiment, detector system is of the photon counting type or of the energy resolving type and capable of defining at least one energy threshold wherein the level crossing frequency is an output count rate for a respective one of the at least one energy thresholds.

In short, what we propose herein is a detector signal processing method based on an exact analytical formulation which constitutes a complete forward model for photon-counting detectors at arbitrarily high flux.

The proposed method allows efficient operation of photon-counting detectors at relatively high flux because the underlying signal model correctly predicts the expected number of counts for a given physical quantity of interest (for instance attenuation, refraction or decoherence/scattering power) in respect of the x-ray beam. In particular pile-up effects are correctly accounted for. Note that, as to "high flux", in a typical clinical CT environment, flux densities up to $10^9$ x-ray photons per $mm^2$ and per s can be reached in and around the unattenuated beam at the location of the x-ray detector.

In an exemplary application of the method, we propose a least-squares decomposition approach to derive material basis images which do not suffer from bias induced by an incorrect pile-up forward model.

The proposed method is of particular applicability in spectral computed tomography where one wishes to quantize measurement data into one or more (e.g. 5) energy thresholds, to decompose the total attenuation into attenuation caused by different materials, e.g. iodine and water, or bone and soft-tissue. The proposed method furnishes a correct forward or backward model to achieve this decomposition. The model-based method can be used for an arbitrary detector response, arbitrarily shaped signal pulses and arbitrary flux and still enables an exact material decomposition.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
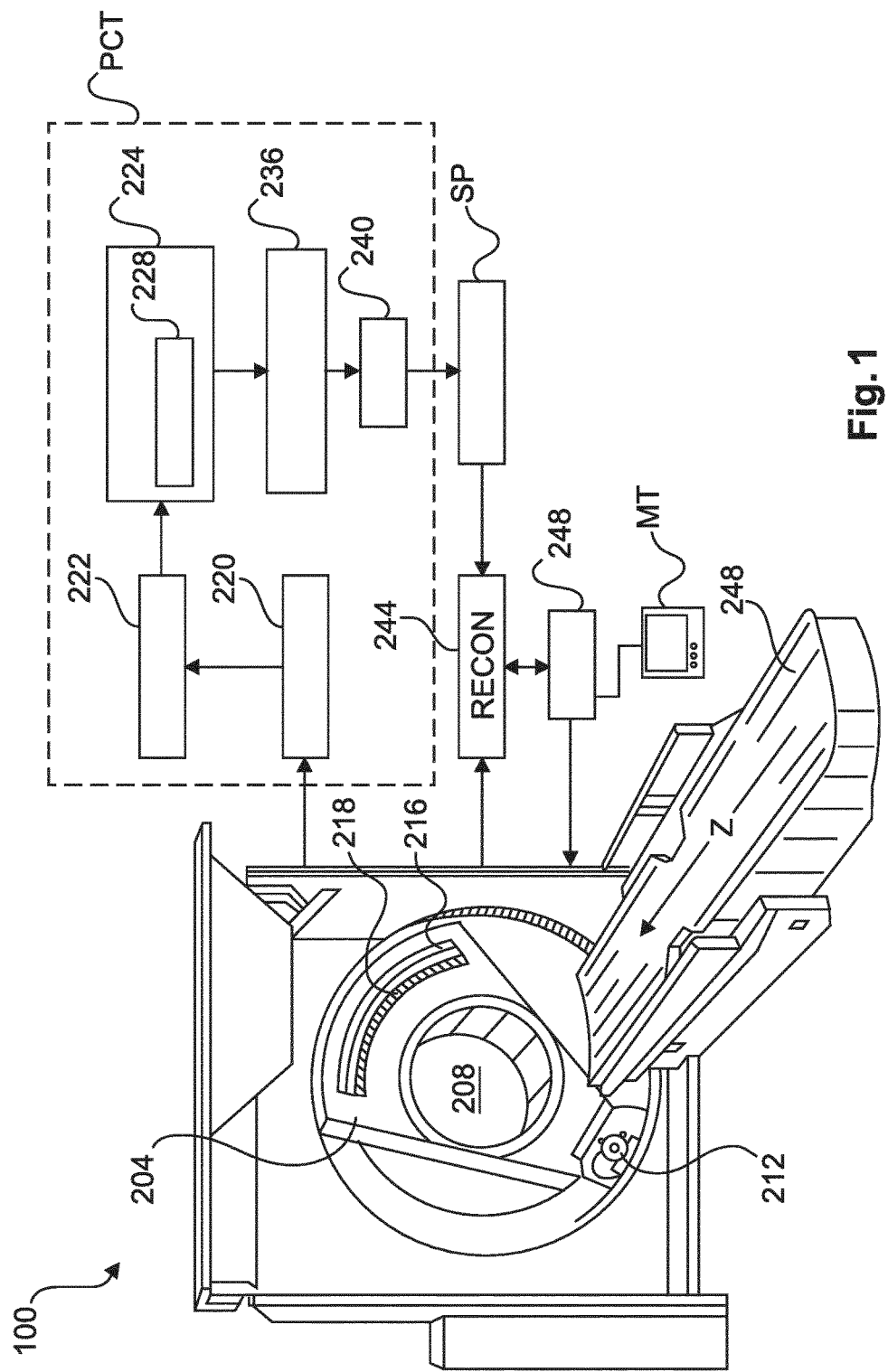
FIG. 1 shows a spectral imaging arrangement.

With reference to FIG. 1, there is shown a spectral imaging arrangement 100. The spectral imaging arrangement includes a computed tomography (CT) system having a rotatable gantry portion 204 that is rotatable about an examination region 208 around a longitudinal or z-axis.

An x-ray source 212, such as an x-ray tube, is supported by the rotating gantry portion 204 and emits a multi-energetic radiation beam or photons that traverse the examination region 208.

A radiation sensitive detector 216 includes one or more sensors or pixels ("cells") 218 that each detects photons emitted by the source 212 that traverse the examination region 208. The sensor 218 generates electrical signals, such as electrical currents or voltages, which are indicative of respective detected photons. Examples of suitable sensors include direct conversion for instance detectors that include a semiconductor wafer portion or body such as a strip, typically formed from Silicon, Cadmium Telluride (CdTe) or Cadmium Zinc Telluride (CZT). Other options are scintillator-based sensors that include a scintillator in optical communication with a photo-sensor.

An object support 248 such as a couch supports a patient or other object in the examination region 208. The object support 248 is movable so as to guide the object within respect to the examination region 208 when performing a scanning procedure. A general purpose computer serves as an operator console 252. The console 252 includes a human readable output device such as a monitor or display and an input device such as a keyboard and mouse. Software resident on the console 252 allows the operator to control and interact with the scanner 200, for example, through a graphical user interface (GUI). Such interaction may include instructions for reconstructing the signals based on the energy-binned data as will be explained in more detail below.

During an imaging session, a specimen (a human or animal patient or parts thereof or any other object of interest (not necessarily organic) resides in the examination region 208. The multi energetic radiation beam having an initial spectrum passes through the specimen. In its passage through the specimen the radiation interacts with matter in the specimen and is as a result of this interaction modified. It is this modified radiation that exits the patient and is then interacting with the detector pixels to produce a corresponding electrical signal. A number of physical processes operate to bring about the change for modification of the radiation in its passage through the matter of the specimen. Notable among those physical processes are absorption, refraction and de-coherence (small angle scattering or dark field effect) . Each of those physical processes can be described by related physical quantities, for instance the local absorption co-efficient $\mu$, the local refraction index $\varphi$, and a small angle scattering power $\Omega$. The mentioned physical quantities, for instance the absorption co-efficient $\mu$ is local because it differs in general across the specimen at each point thereof. More particularly the absorption view is a function of the type of material (fat, bone or other material) and the density thereof at that point. Furthermore, there is also an energy dependence of for instance the absorption $\mu$. Alvarez and Macovski have written extensively on this ("Energy-selective Reconstructions in X-ray Computerized Tomography", PHYS. MED. BIOL., 1976, VOL. 21, NO. 5, 733-744). It is known that the attenuation or absorption coefficient $\mu$ varies with the energy in a manner that is characteristic of the elemental composition of the material. In other words, the x-ray energy spectrum as emitted undergoes a characteristic "coloring" during its passage through the object. One can also express the overall attenuation through the specimen along a path as a linear combination of material specific attenuation coefficients and the respective line integrals through the respective material in the specimen. See eq (1), p 1250 in C Schirra et al in "Statistical Reconstruction of Material Decomposed Data in Spectral CT", IEEE Trans on Medical Imaging, vol 32, No 7, July 2013. It is these facts that one tries to harness in spectral CT imaging to arrive at distinctive images for each of the material basis elements of interest and the overall task is to resolve the detected signals into the various material specific line integrals. In other words, the electric signals detected at the detector are spectrally analyzed in a manner to be described in more detail below. The spectrally processed data is then forwarded to a re-constructor 244 that operates to reconstruct the processed data into characteristic images for each of the different materials. In other words, an elemental decomposition is achieved as reconstructor 244 selectively reconstructs the signals generated by the sensor 118 based on the spectral characteristics of the detected photons. For example, the binned data can be used to generally isolate different types of organic materials having different photon absorbing characteristics such as bone, organic tissue, fat and/or the like, locate contrast enhancement materials, and/or otherwise process the detected signals based on spectral characteristics. Because the specimen is exposed to radiation across different projection directions during the rotation of the x-ray source a cross sectional representation of the interior in respect of the material of interest can be reconstructed.

The energy spectrum information is extracted through a pulse height analysis PHA. The PHA is implemented in the FIG. 1 embodiment via a photon counting circuitry PCT. The PCT circuitry interacts with the various detector cells in detector 216. Each of the photons of the modified x-ray beam has a specific energy. This energy can be related in direct proportion to an electrical pulse, more specifically of a pulse height. Yet more specifically when a certain photon interacts with the (highly depleted) semiconductor body of the detector cell 218, a certain number of electron-hole pairs are generated. The number of electron-hole pairs so generated is in direct proportion to the energy of the interacting photon. A relatively large bias voltage is applied across the semiconductor body of the detector cell. The bias voltage causes the electron and holes to be diffused away from each other. Holes and electrons are then collected at the respective electrodes at opposite sides of the detector cell. This collection then gives rise, as a function of the number of so defused electron-wholes pairs, to a characteristic current or voltage pulse height at read out channel of the pixel's electrodes. The electronic pulse generated in the detector cell is then processed by the photon counting circuitry PCT in the following manner:

A pre-amplifier 220 amplifies each electrical signal generated by any of pixels 218.

A pulse shaper 222 processes the amplified electrical signal for a detected photon and generates a corresponding analog signal that includes a pulse such as a voltage or other pulse indicative of a detected photon. The so generated pulse has a predefined shape or profile. In this example, the pulse has peak amplitude that is indicative of the energy of the detected photon.

An energy-discriminator 224 energy-discriminates the analog pulse. In this example, the energy discriminator 224 includes a plurality of comparators 228 that respectively compare the amplitude of the analog signal with a threshold that corresponds to a particular energy level. Said differently, discriminator 224 operates to determine "height" of the incoming pulses as generated by shaper 222. More specifically, each comparator 228 produces an output signal that is indicative of whether the amplitude of the pulse exceeds its threshold. In this example, the output signal from each comparator produces a digital signal that includes a transition from low to high (or high to low) when the pulse amplitude increases and crosses its threshold, and from high to low (or low to high) when the pulse amplitude decreases and crosses its threshold.

In an exemplary comparator embodiment, the output of each comparator transitions from low to high when the amplitude increases and crosses its threshold and from high to low when the pulse amplitude decreases and crosses its threshold.

A counter 236 counts the rising (or in some embodiments the falling) edges respectively for each threshold. The counter 236 may include a single counter or individual sub-counters for each threshold. An energy binner 240 energy-bins the counts into energy ranges or bins corresponding to ranges between the energy thresholds. The binned data is used to energy-resolve the detected photons.

In other words, the PCT signal processing chain operates to quantize the pulse height of each incoming pulse into the energy bins defined by the number of voltage thresholds. N (N at least 1, preferably at least 2) (voltage, amperage or other Energy indicative) thresholds are capable of defining, N energy bins for recording pulse heights higher than respective ones of said threshold. For instance, a pulse whose edge rises beyond (that is "crosses") two of said thresholds will elicit a count for each of the two bins associated with the respective two thresholds. If only the lower one of the threshold is crossed, there will be only one count, etc. But this is an example only as in some embodiments only falling edges elicit counts or both, rising and falling edges elicit counts. Said differently the PCT circuitry furnishes at its output a number of counts in each bin, a histogram as it were. That is, PCT circuitry records in a certain timeframe the number and height of all pulses that the modified x-ray beam has caused in its interaction with the detector electronics. The recorded photon counts in each bin (1, 2 or preferably more like 3 or 5 energy bins are envisaged herein) are then forwarded to the spectral analyzer SP.

Figure 2:
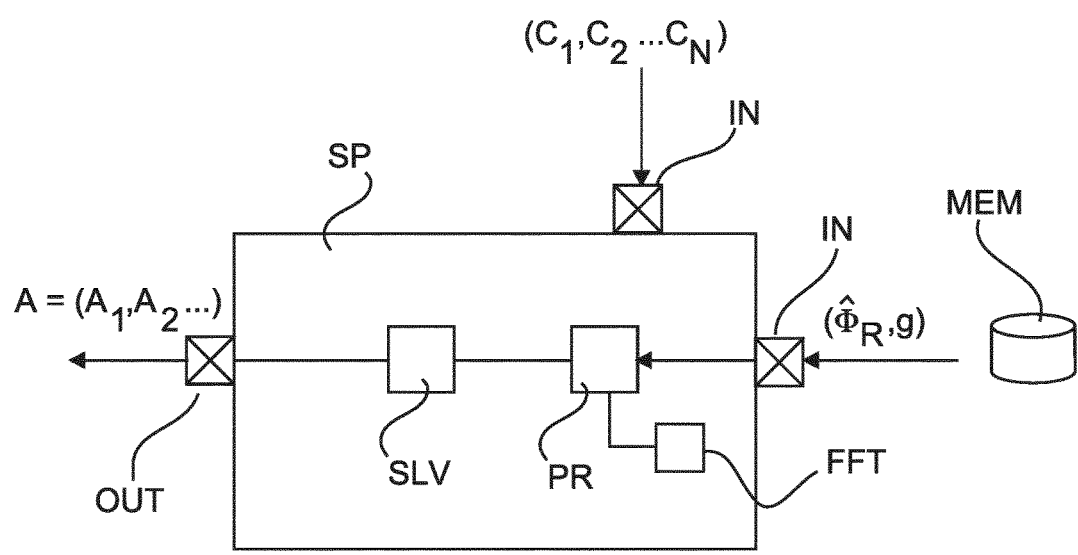
FIG. 2 shows a signal processing component of the arrangement as per FIG. 1.

Components of the spectral analyzer are shown in more detail in FIG. 2. Broadly, spectral analyzer SP comprises an input port IN and an output port OUT. The spectral analyzer SP comprises two modules, a predictor PR and a solver SLV. There is also a fast Fourier transform component FFT that answers fast Fourier transformation requests by predictor PR or solver SLV. Fourier transform component FFT may also be used to compute an inverse fast Fourier transform. There is also a memory MEM on which specifications of the detector electronics are stored.

Predictor module PR reads in the detector specifications and includes same into a functional description of a forward signal model. The forward signal model predicts, that is computes, the average count rate for each bin given a certain material combination in the sample or specimen. More particularly, the predictor computes for any one of the different energy thresholds, the conditional expectations of registering a pulse that crosses said threshold, given the operation of one or more of the physical effects of interest caused by the presence of one or more different material types in the sample. In other words, the conditional expectation is expressed in terms of parameters for each of the physical effects of interest. Said parameters are free parameters and can be adapted in a fitting operation to the actually observed for photonic counts $c=(c_1, c_2, \ldots, c_N)$. More particularly the observed photon counts are received at input port IN. The received photon counts are combined with the model to formulate an objective function. The objective function is then solved for the physical quantity parameters of interest by solver SLV. The solved for parameters for the physical quantities A are then output at output port OUT. The objective function is essentially a measure to quantify a deviation between the observed counts and the expected counts as per the signal model. The expected counts may be formulated in terms of the parameters for the physical quantities A of interest and the solver SLV operates to compute said parameters so as to minimize said deviation to thereby solve for said parameter of interest. Formulation as a minimization problem is an exemplary embodiment only and alternative formulations in terms of a maximization problem may be called for in other contexts.

In one embodiment the so output physical parameters describe the material characteristic attenuation co-efficient. In other words, the output is in general a vector with each entry describing the respective physical quantity (such as the attenuation coefficient) for a given material type. Broadly looked at, the signal processor SP implements a model based transformation from observed count rates acquired at a given projection direction into projections along said direction of a physical quantity of interest. Again, this physical quantity A may be the material specific absorption coefficient or may be the refraction index or the scattering power as the case may be. The used model as proposed herein obviates previous attempts in literature to merely approximate pile up behavior. The model as proposed herein presents an exact analytical formula which constitutes a complete forward model for photon counting detectors at arbitrary high fluxes. In other words, the analytic model as proposed herein correctly models pile up effects. In particular no pile up correction modules as used previously, are necessary because the pile up effects are correctly accounted for in the model. Of course, this does not exclude the use of the proposed model based approach in pile-up correction schemes which might be beneficially used for other reasons.

Figure 3:
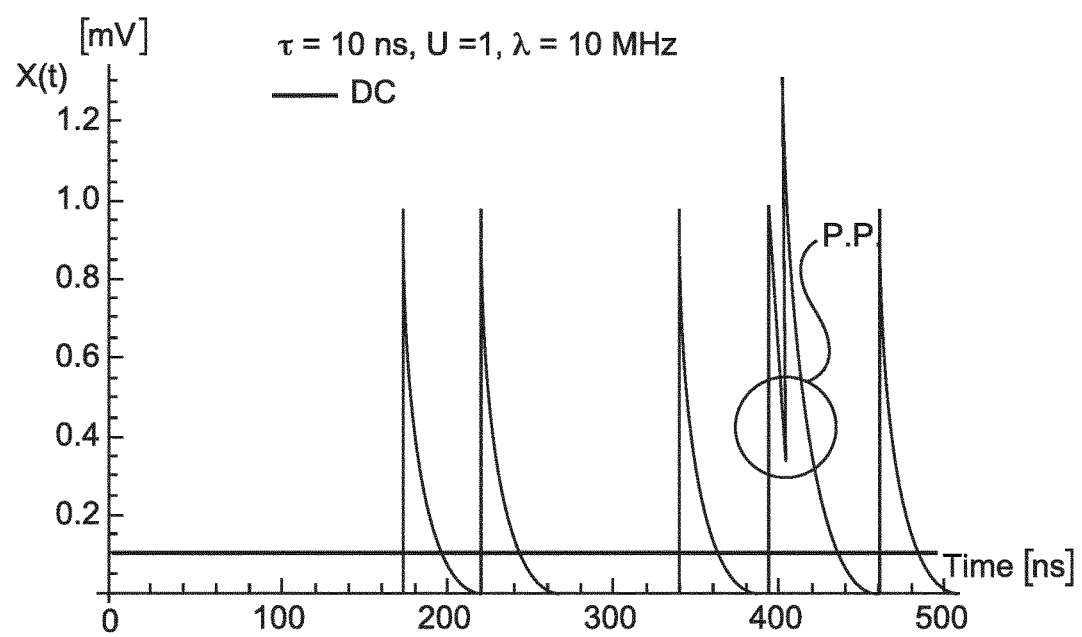
FIG. 3 illustrates pulse pile up.

The graph in FIG. 3 illustrates the pile up effect. The graph shows a pulse train of different pulses as output by pulse shaper in response to photon interactions in the semiconductor body of the detector. For clarity and for purely illustrative purposes, pulses of same heights are shown which, of course, is not the case in reality as the pulse heights themselves are varying at random with photon energy. A pile up occurrence is indicated in circle PP. The pile up event occurred at about 400 nanoseconds. Pile up happens if pulses arrive closer in time than the pulse resolution time capabilities of the detector electronics admits. In other words, as can be seen the second, later pulse "rides" on the tail of the earlier pulse to form a combined pulse. But the combined pulse is higher than each of the pulses it is combined from. This leads to "doubly" false readings as i) an incorrect number of pulses are recorded (two pulses are recorded as one) and ii) an incorrect pulse height is recorded (the pulse height is overestimated due to "wrong" superposition). This can cause severe artifacts in images that are reconstructed from such pulse inflicted count data (also referred to herein as OCR, i.e. "output-count-rate").

Figure 4:
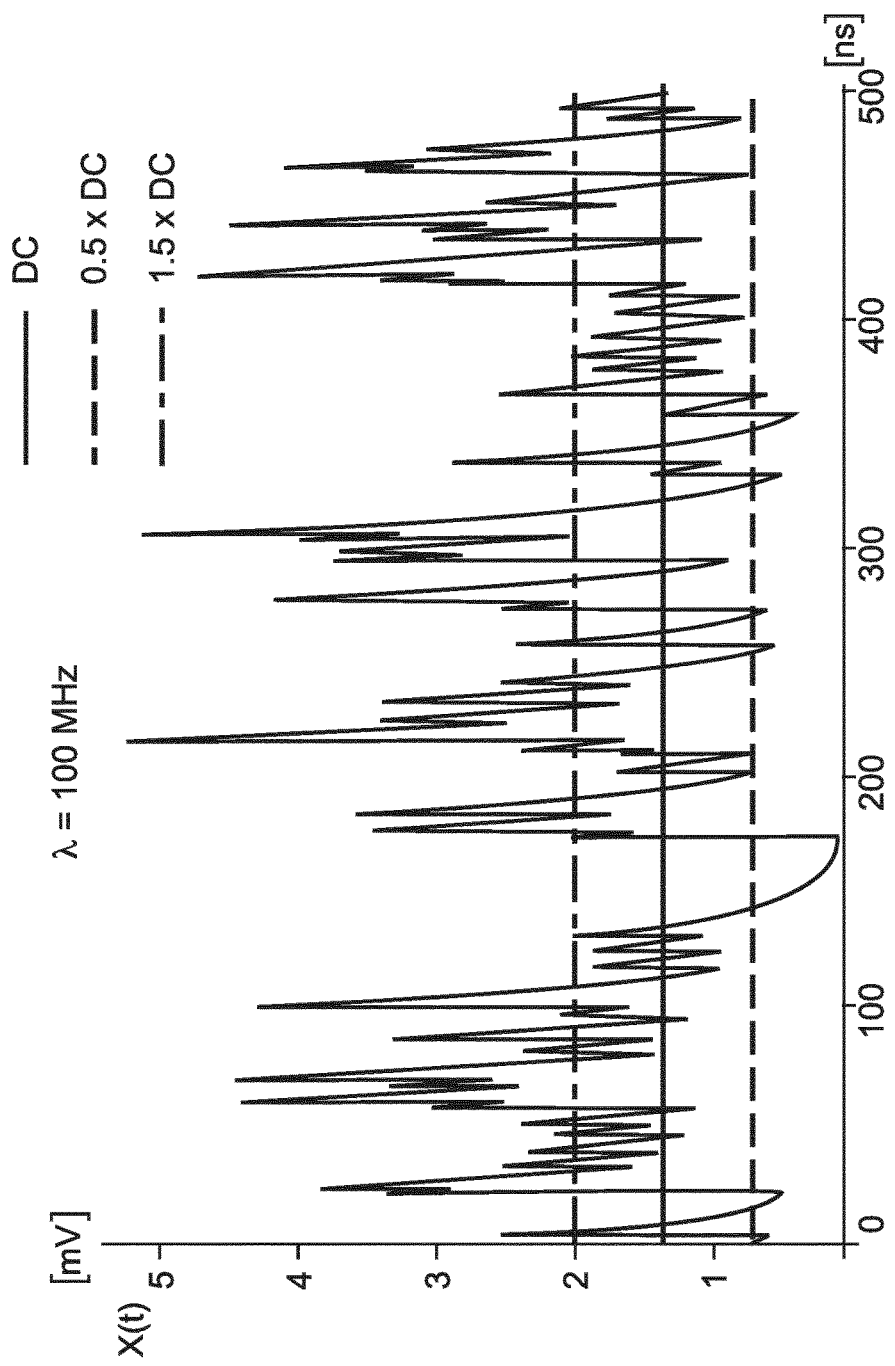
FIG. 4 illustrates threshold based photon counting.

FIG. 4 illustrates a more realistic example, that is, each instance of a pulse corresponds to a photon interaction event and the pulse height of each pulse varies with the energy of that photon. Also, FIG. 4 illustrates the case of a PCT electronics that interrogates the incoming pulses for three threshold levels, shown as DC, 0.5 times DC and 1.5 times DC to so define three different energy bins (pulses below 0.5 will not be detected) into which the counts c will be binned. As can be seen, the recorded count will be heavily distorted due to the high rate at 100 Mhz and consequently the many pulse pile ups. Again, any number of one or more thresholds are envisaged herein, the 3 thresholds in FIG. 4 being purely illustrative.

The graphs in FIGS. 3,4 are suggestive of a time series or train of pules. However, the time series itself is not observed by the detector but it is only the count events that are observed. It turns out that is nevertheless useful as shown herein to consider the "peaks" of the pulses as elements mapped into the voltage-time diagram as per FIGS. 3,4 for instance and to consider the "dynamics" of those peak points. It has been shown that the peak point dynamics can be modeled as a doubly stochastic process X(t). The process is "doubly" stochastic because it uses i) one probability density to model the distribution of inter-pulse intervals along the time axis (that is, intervals between two consequent pulse events) and ii) a second probability density to model independently from said intervals the pulse height U which itself is an independent random variable. One can then consider the dynamics of the peak points in the voltage-time plane. One can then ascribe a "velocity" "X dot" to the peak points. It is then possible to study the level crossings of said peak point in unit time. Taking his heuristics further, one can define a neighborhood around each of the level. If one knows the velocity of the peak point within said neighborhood one may then relate the velocity to the expected crossings of the respective level. A formulism similar to this has been proposed previously in the 1940's by O. Rice who studied shot noise, more particularly he studied level crossing frequency of the stationary ergodic process involving the joint probability distribution $p(X(t)), \dot{X}((t))$ of a dynamic process X(t) and "X dot" its time derivative t. See S. O. Rice, Mathematical Analysis of Random Noise, Bell Systems Tech. J., Volume 24, p. 46-156, 24:46-156, 1945.

Applicant has found that the probabilistic dynamics of shot noise describes exactly count events in the detector electronic of photon counting devices. Applicant has discovered by experiments that the pile-up phenomenon is mathematically identical to shot noise and the counting result of energy sensitive x-ray detectors can be identified with the frequency of level crossings for shot noise processes. A rather recent mathematical publication (H Biermé and A Desolneux, "A Fourier Approach for the Level Crossings of Shot Noise Processes with Jumps", Journal of Applied Probability, 49(1):100-113, 2012) has revealed that level crossings of shot noise processes become mathematically more tractable if one considers the Fourier transforms of the level-crossing frequency, rather than the considering the frequency itself. Taking advantage of this simplification in Fourier space, an analytic expression of the forward (or backward) signal model after an inverse Fourier transformation (see the outermost integral) back into the space of pulse heights U can be written as follows:

$$N_X(U, A) = \int_{-\infty}^{\infty} e^{-iuU} \int_0^{\infty} \hat{\Phi}_R(E, u) D(E) \Phi_0(E) e^{-\sum_{\alpha=1}^N \mu_\alpha(E) A_\alpha} \quad (1)$$
$$dE \cdot \exp\left(-\int_0^{\infty} \hat{K}(E, u) D(E) \Phi_0(E) e^{-\sum_{\alpha=1}^N \mu_\alpha(E) A_\alpha} dE\right) du$$

In the above Eq. $N_X(U, A)$ denotes the expected rate of registered counts for a given energy threshold U and a given attenuation A by the object. D(E) is the detector absorption efficiency, $\Phi_0(E)$ the x-ray source spectrum. $\hat{\Phi}_R(E, u)$ denotes the Fourier transform of the cumulative detector response function, $\mu_\alpha(E)$ is the linear attenuation coefficient of basis material α and the "pile-up kernel" $\hat{K}(E, u)$ is given by:

$$\hat{K}(E,u) = -i\int_{-\infty}^{\infty} ug(t) \hat{\Phi}_R(E, u\, g(t)) dt \quad (2)$$

The above pile-up Kernel (2) correctly describes the complicated, linear superposition of an arbitrary number of pulses at energy E and predicts the modifications due to pile-up of the number of times, the analog output of the detector signal passes the threshold at pulse-height U per unit of time.

What the kernel operation (2) does is to integrate over time the pulse shapes over time each weighted by the Fourier transform of the cumulative detector response. In equation (1) upper case U indicates pulse height space, (for instance expressing voltages) whereas lower case u indicates the frequency variable of pulse height U in Fourier space as per the following Fourier definition $$N_X(U) = \frac{1}{2\pi} \int_{-\infty}^{\infty} e^{-iuU} \hat{N}_X(u) du,$$

with $N_X(U)$ denoting the expected cross rates of level U by process X(t). In other words, the model eq (1) is expressed in terms of the variable u in Fourier space. u represents the frequency variable in Fourier space related to U.

The underlying doubly stochastic modeling of the sequence of pulse peaks is given by $$X(t) = \sum_{i \in \mathbb{Z}} U_i g(t - t_i),$$

where X is random variable of the previously sketched doubly random process, with the t, being Poisson points following a random exponential Poisson distribution in time and the pulse heights random variable U having spectrum p(U) in the space of pulse heights with $U_i$ independent for different i but equally distributed. The quantity g "imprints" the pulse shape and is determined by the electronics of the pulse shaper in the PCT. Exemplary pulse shapes are $g(t) = e^{-t/\tau}$ (t>0), with τ the typical pulse duration but other pulse shapes such as rectangular ones of length a and height $U_0$ are also possible.

Extending the results of Biermé et al, it has been found by Applicants that the complex superposition of the pulses by pile-up can be "entangled" in Fourier space by considering the Fourier transform $\hat{F}(u)$ of the pulse height spectrum p(U). It turns out that the Fourier transform of $N_X(U)$ can be expressed as a sum of responses of the Fourier transformed spectrum p(u) at instances ("jumps") where the rising pulse edges occur. The sum of responses at said jumps is weighted by a velocity component that incorporates the Fourier transform of the joint probability density p(X, Ẋ). See expression 7 on page 6 in Biermé.

The application of the shot noise context to the present behavior of detector electronics for photon counting purposes is driven in parts of Applicants recognition, that the pulse height density p(U) can be expressed via the detector response R(E, U) as $$p(U) = \lambda^{-1} \int_0^\infty R(E, U) D(E) \Phi(E) dE,$$

Translating this into Fourier space as per $\hat{F}(u)$ mentioned above then yields the desired simplification of the pulse-pile up superpositions.

Equation (1) in the form given above makes explicit the dependence of the expected rate of registered counts on the attenuation basis $\{\mu_\alpha(E)\}$ and the corresponding basis material line integrals $A=(A_\alpha)$. This is achieved by introducing the photon fluence $\Phi_0$ of the source in units of photons per mAs sr keV, with sr steradian. In other words, the signal forward model as per equation 1 has been written out by conditioning the expected OCR on the physical quantity of interest, in this exemplary case, the attenuation. A similar formula can be drawn up for each of the other physical quantities of interest, namely the refraction φ for phase contrast imaging and the decoherence scatter for dark field imaging. Also the pulse height is represented as voltages herein, however, this may not necessarily be so in other contexts and amperages of other suitable observables may be used instead to express or quantify the OCR.

From the structure of equation 1 one can see it comprises an inverse Fourier transformation (this is the outer integral) of a product of two Fourier integrals. Each component of the signal model includes the Fourier transform $\hat{\Phi}_R(E, u)$ of the cumulative responsive function $\Phi_R(E, U)$ which measures the mean number of pulses registered per event of energy E with pulse heights larger than U. The cumulative responsive function $\Phi_R(E, U)$ can be readily measured during a threshold scan at low fluence with a mono-chromatic input x-ray as has been described elsewhere by Schlomka et al ("Experimental feasibility of multi-energy photon-counting K-edge imaging in pre-clinical computed tomography", Phys. Med. Biol. 53 (2008) 4031-4047) on page 4037 in section 4.1. The Schlomka reference is incorporated herein by reference in its entirety.

As the structure of the signal model as per equation 1 reveals the main input components are the detector electronic specifications. More specifically, once the detector absorption efficiency D and the x-ray source spectrum Φ is known, all that there remains to specify is the (Fourier transform of the) cumulative response function $\hat{\Phi}_R(E, u)$ and the pulse shape function g(t) as output by pulse shaper of the PCT circuitry as described earlier pulse shaper in FIG. 1. Once these quantities are given, the model (1) can be set up in terms of the physical quantity of interest for instance in this case the attenuation context where the respective physical parameters are the projections of the absorption coefficients that is the line integrals A for each of the base materials α.

An analysis in taking limits in eq(1) reveals that for low photon fluence (or high attenuation, or both), the exponential term involving $\hat{K}$ (E, u) approaches unity and a low flux expectation is recovered as per:

$$N_X^{low\ flux}(U, A) = \int_0^\infty \Phi_R(E, u) D(E) \Phi_0(E) e^{-\sum_{\alpha=1}^N \mu_\alpha(E) A_\alpha} dE \quad (3)$$

Also, the structure of eq (1) is basically that of a Fourier transform of a product of two functions so eq (1) can be rewritten as a convolution in pulse-height space of the "low flux" expectation eq. (3) and the Fourier transform of the exponential term in eq (1) (the latter reduces to a delta function for low fluence), in other words:

$$N_X(U,A) = (N_X^{low\ flux} \otimes L)(U,A) = \int_{-\infty}^\infty N_X^{low\ flux}(U',A) \cdot L(U-U',A) dU' \quad (4)$$

With $$L(U,A) = \int_{-\infty}^\infty e^{-iuU} \exp(-\int_0^\infty \hat{K}(E,u) D(E) \Phi_0(E) e^{-\sum_{\alpha=1}^N \mu_\alpha(E) A_\alpha} dE) dU \quad (5)$$

Figure 5:
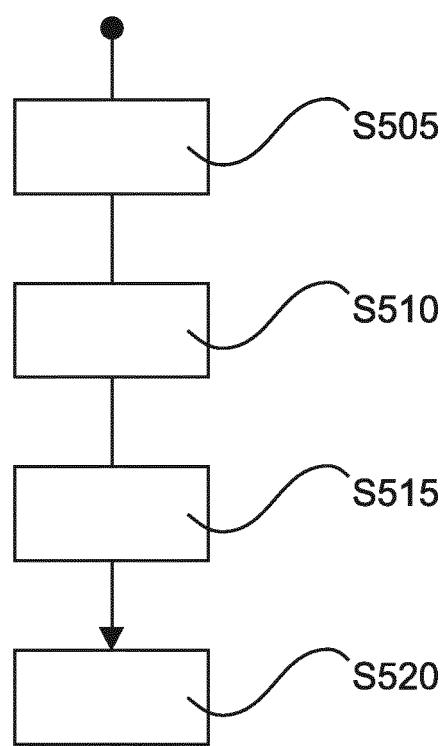
FIG. 5 shows a flow chart of a signal processing method.

Operation of signal processor SP will now be explained with reference to flow chart as per FIG. 5.

At step S505 detector electronic specifications are read in. Detector specifications include in particular the cumulative response function and a function description of the pulse shape as delivered by pulse shaper of the detector electronics used for acquiring the photon count data c. The cumulative response function and/or the pulse shape description is then Fourier transformed. The Fourier transformed detector specifications are included in the model as per equation 1 above to initialize same with the currently used detector electronics.

The model may be set up as a forward model to include suitable material specific parameters of interest that reflect the physical quantity which one wishes to reconstruct for in a material decomposition operation. According to one embodiment the parameter A formed from the material specify attenuation coefficients and or the respective line integrals along respective X-ray source-detector pixels paths through the sample thought to be made up from the various basis materials.

At step S510 the actual OCR counts, that is the counts per bin, are received.

At step S515 a fitting operation is performed in order to fit the physical quantity parameters of the model to the received OCR counts. In one embodiment the predicted (as per model 1 (1) level crossing rates are related via an objective function to the actually observed count rates c. In one implementation embodiment of the spectral forward model as per eq (1), the Fourier transform expressions $\hat{\Phi}_R(E,$ u) and $\hat{K}(E, u)$ can be pre-computed and held in memory MEM for retrieval on-demand as they are independent of the attenuation or the respective physical quantity of interest. To compute the expected number of counts (for each threshold U) given a certain attenuation A, two integrations over the energy (for every u in Fourier space) and one Fourier transform are required. However, the first integration over the energy in Eq. (1) can be postponed until after the Fourier transformation, saving computation time. Also, the Fourier transformation may not need to be computed for each value of U but only for those thresholds of interest in a given situation. In other words, the proposed methods may include a pre-selection step to establish the thresholds of interest (that is for instance those thresholds that have actually been set up in the PCT electronics) and the FFT component is then instructed accordingly.

The output of fitting step S515 is a set of physical parameters that together define a transformation from the received bin counts to the set physical parameters for a given projection direction and/or path.

The fitting operation S515 is performed for each projection direction and detector element. The objective function at Step S515 can be solved for the desired physical parameters by any suitable optimization algorithm such as least-squares or maximum-likelihood (which requires a suitable noise model, e.g. Gaussian or Poisson) etc.

More particularly, the fitting step S515 is in particular repeated for each possible path from the radiation source to the respective detector pixel. In other words, a set of physical parameters per base material is computed for each detector pixel.

The association between pixel and path is furnished by the imager's control electronics which tracks the changing imaging geometry and stamps each set of counts with the respective projection path. The so computed physical parameters A are then forwarded to Step S520 where a reconstruction algorithm such as filtered back-projection or otherwise is applied to each of the physical parameters per base material to arrive at a plurality of different cross sectional images, one for each material. In the following, an example will be given where the physical quantity is the absorption per base material.

In an exemplary embodiment, we propose a decomposition technique based on the above forward model in the following way. Let $m_i$ denote the measured value of counts for the threshold $U_i$ and let $U_1 \ldots U_M$ be M different energy thresholds of the energy-sensitive photon counting detector. Then, we can estimate the material line-integrals A from the following least-squares approach by minimizing the following functional (or objective function) with respect to A:

$$\chi^2(m_i, A) = \sum_{i=1}^{M} \left( \frac{m_i - N_X(U_i, A)}{\sigma_i^2(U_i, A)} \right)^2.$$

The least-square estimate is then formally given by:

$$\hat{A}^{L.S.} = \mathrm{argmin}_A \chi^2(m_i, A).$$

In the above equation, $\sigma^2_i(U_i, A)$ are the variances of the measurements $m_i$ and those depend in general on the pulse height threshold $U_i$ and on the attenuation A, as does the expectation itself. Since, however this effect is of second order, a simplified model for the variances might suffice to reliably estimate the material line-integrals, e.g., the Poisson approximation:

$$\sigma^2_i(U_i, A) \approx N_X(U_i, A).$$

Alternatives to the least-squares approach are of course also possible as potential estimators, like a maximum-likelihood approach with Gaussian or Poisson noise model.

It will be appreciated that the signal model as per FIG. 1 has been used as a forward model herein, in other words, the counts are predicted given the physical quantity of interest (absorption, refraction or dark field scatter). The model in equation 1 can also be looked at as a backward model wherein the physical quantity is predicted given counts. Also equation 1 has been written in dependence on specific physical quantity of interest, namely absorption. However, this is purely illustrative purposes only and it is a matter of notation to re-write the model of equation 1 in terms of physical quantities of interest, for instance, refraction and face contrast imaging or de-coherence for dark field imaging. The accuracy of the proposed model allows pulse height analyzing, counts at substantially any fluence. More particularly, if one were to compute a reference image using the above method for a given physical quantity and if one were then to compare this image with a sequence of other images processed at different fluence rates one will observe that the mean bias for those images will be minimized in both cases which is not the case when known, merely approximate models for the expected number of counts are used. This demonstrates the usefulness of the proposed modeling scheme and signal processing method across the fluence spectrum.

Figure 6:
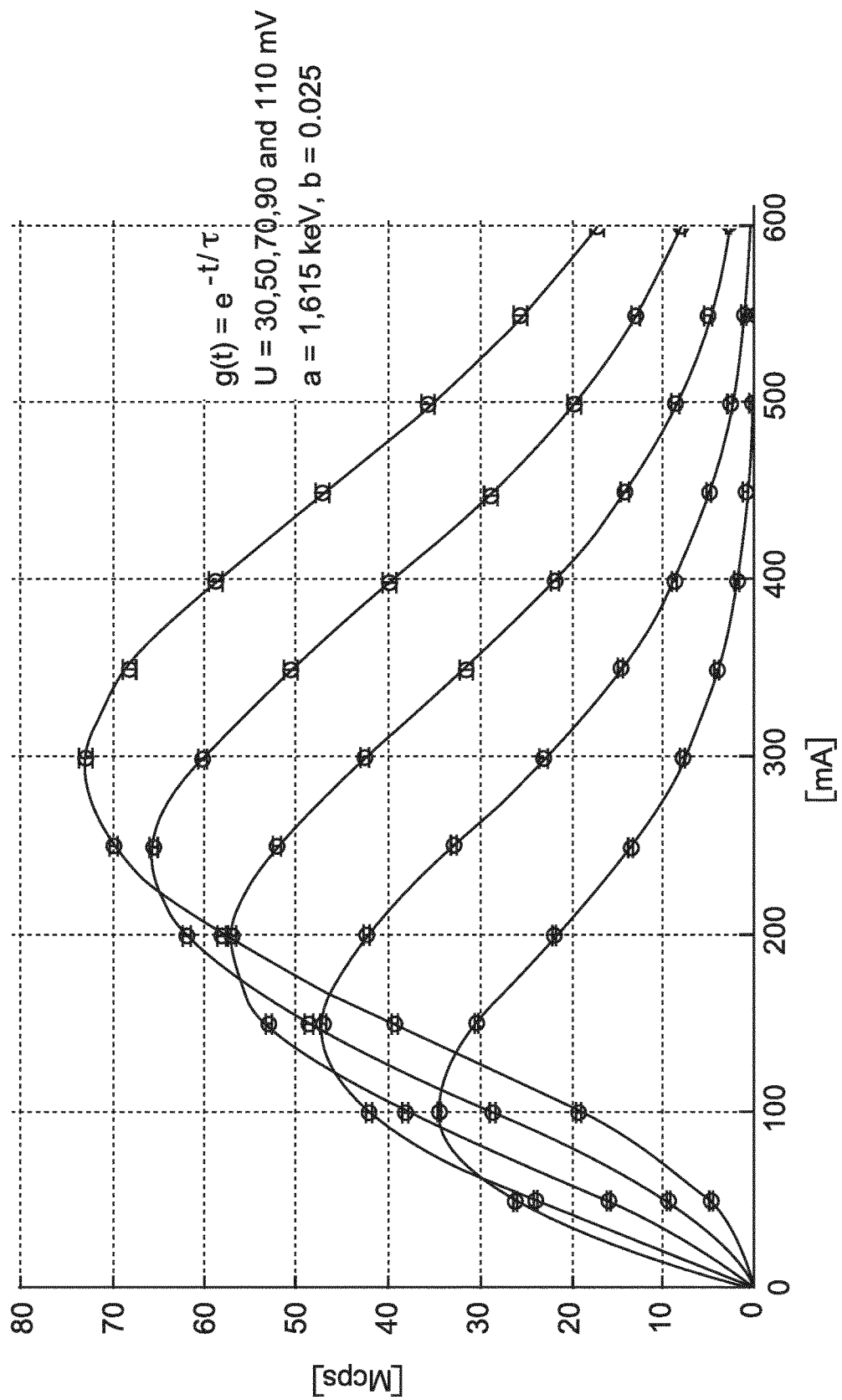
FIG. 6 shows an analytical prediction of photon counts according to the proposed method compared to simulation results.

We attach FIG. 6 to corroborate the exactness of the proposed method by numerical data obtained via a Matlab suite computation. More particularly, a Monte-Carlo (MC) simulation has been run to produce different data sets. As can be seen in analytical predictions using the above model and the simulation results substantially coincide. The curves show level crossing frequency rate in Mcps on the vertical axis versus tube current in mA on the horizontal axis. The disc markers indicate the course of the simulation and the solid lines indicate the analytical result. More particularly, the model-based analytical predictions and Monte-Carlo simulation of the expected number of counts registered in a photon-counting detector for 5 different values of the energy threshold U=30 keV, 50 keV, 70 keV, 90 keV and 110 keV are plotted as a function of anode tube current for a detector spanning a solid angle of $\Omega=10^{-6}$ sr.

Figure 7:
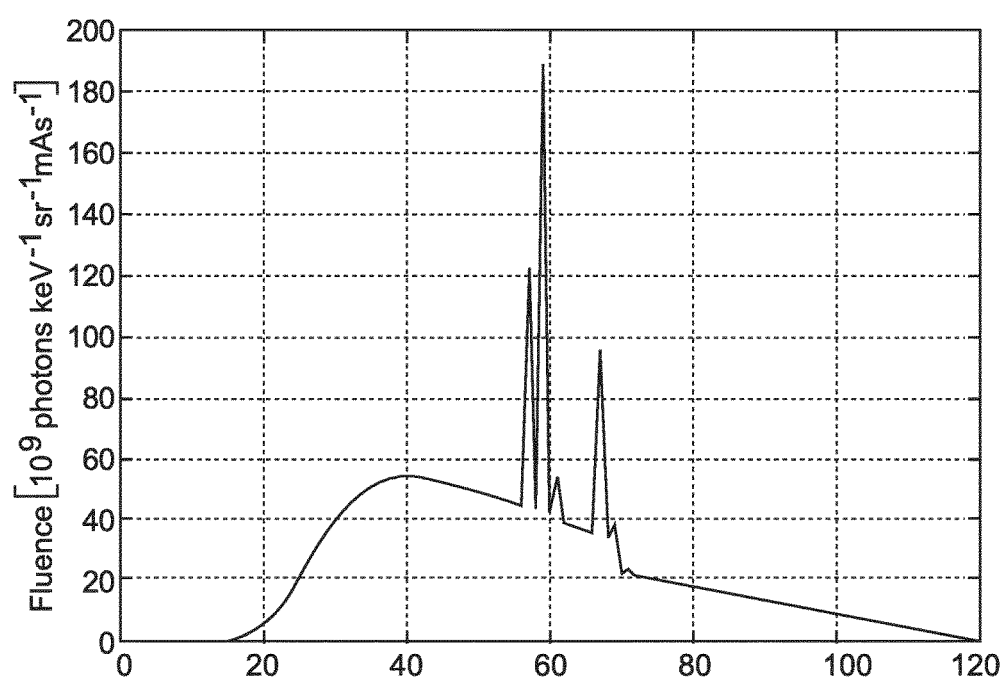
FIG. 7 shows a fluence spectrum of radiation as used in the simulation as per FIG. 6.

The error bars represent five standard deviations of the MC simulations' statistical error (with 1 mV corresponding to 1 keV in the simulation), a Gaussian detector response with FWHM as in the Schlomka reference (That is, FWHM=a+bE, with a=1:615 keV, b=0:025 and E being the energy in keV). The x-ray fluence spectrum is shown in FIG. 7. Pulse shapes were taken of the exponential form as described above, $g(t)=e^{-t/\tau}$ for positive t and zero otherwise, with $\tau=10$ ns.

The number of noise realizations and the number of pulses per realization and data point were both chosen to be 1000. The error bars represent five standard deviations of the MC simulations as obtained from the sample variance over the 1000 realizations. The remaining deviations are very small and due to the use of the discrete Fourier transforms with finite length.

To summarize, what we propose herein is an analytic forward or backward model for energy-sensitive, photon-counting detectors for arbitrary detector response, pulse shapes and arbitrarily high x-ray fluence. The expected number of counts per unit of time is described by means of a Fourier integral, or by means of a convolution of the low-fluence expectation and a pile-up kernel. The Monte-Carlo simulation as per FIG. 6 verifies the validity of our results.

Although the above method steps have been explained at the example where the physical quantities are the material specific attenuation coefficients, this in for illustrative only and the method can be readily adapted for spectral phase contrast or spectral dark field imaging. For instance, to account in model (1) for phase shift and/or scattering power, one expands the complexity of the model by multiplying the absorption model term $$e^{-\Sigma_{\alpha=1}^{N}\mu_{\alpha}(E)A_{\alpha}}$$

by the model expression $$(1+V(E)e^{-\Omega f_{DC}(E)}F(\alpha(E)\Delta\varphi),$$

where V(E) is the visibility (of an interferometer), $\Omega$ is the scattering power along the line of sight, $f_{DC}$ the energy dependence of the latter small angle scattering, and $\Delta\varphi$ relates to the phase shift caused by the refraction with a being an energy dependent factor. F( ) is a trigonometric function (such as a sinusoid) to model the intensity modulations caused by the sample induced refraction upon phase stepping, or upon any other interferometric measure, phase stepping being one exemplary embodiment. The energy integration in eq (1) will need to be extended through each of the energy dependent terms in the expanded model.

In the model as per eq (1) a mono-polar pulse structure has been assumed. In other words, the pulse is always positive or always negative. However, eq (1) may be reformed to account for bi-polar-pulses with both, positive and negative parts. In general the above approach is valid for pulses that can be approximated by step functions.

Also, in the above model a count is defined by registering the rising pulse edge only but the model is of equal application for falling edges.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A method comprising:
   detecting a signal after passage of radiation through a sample with an energy resolving detector;
   measuring a count rate for photonic interactions with the detector from the signal;
   receiving the measured count rate;
   fitting a signal model to the measured counts, wherein the signal model is configured to account for a pulse-pile-up effect, the signal model representing a conditional expectation of a frequency of at least uni-directional pulse crossing of at least one energy level, given a physical quantity of a material in a sample, wherein the signal model incorporates a Fourier representation of a pulse height variable.

2. The method of claim 1, wherein the fitting operation includes solving an objective function based on the model for a parameter for the physical quantity.

3. The method of claim 1, wherein the signal model incorporates a Fourier transform of a cumulative spectral response function of the detector.

4. The method of claim 1, wherein the count rate is registered as one or more electronic pulses detected at an instant, the one or more pulses having a pulse height and wherein the signal model is based on a description of a random process for the one or more pulses, wherein the random process model is formed from two probability densities, one for a distribution of intervals between two consecutive pulses and the other for the distribution of the pulse height.

5. The method of claim 1, wherein the physical quantity is any one of absorption, refraction or scatter.

6. The method of claim 1, wherein a fidelity of the solved for parameters for the physical quantity is independent of a photon fluence of the radiation.

7. The method according to claim 1, wherein a signal measured by an energy-resolving detector is processed after passage of radiation through a sample.

8. The method of claim 3, wherein the Fourier transform is pre-computed.

9. The method of claim 4, wherein the random process model is that of shot noise.

10. The method of claim 6, wherein, the signal model includes a functional description of pulse shape.

11. A method comprising:
detecting a signal after passage of radiation through a sample with an energy resolving detector;
measuring a count rate for photonic interactions with the detector from the signal;
receiving the measured count rate;
fitting a signal model to the measured counts, wherein the signal model represents a conditional expectation of a frequency of at least uni-directional pulse crossing of at least one energy level, given a physical quantity of a material in a sample, wherein the fitting operation includes solving an objective function for a parameter for the physical quantity,
wherein a fidelity of the solved for parameter for the physical quantity is independent of a photon fluence of the radiation.

12. The method of claim 11, wherein the detector is of the photon counting type and capable of defining at least one energy threshold wherein the level crossing frequency is an output count rate for a respective one of the at least one energy thresholds.

13. The method according to claim 11, wherein a signal measured by a photon-counting detector is processed after passage of radiation through a sample.

14. A non-transitory computer readable medium having stored thereon a computer program product, comprising computer readable code to control a signal processing apparatus which, when being executed by a data processing circuitry, is adapted to perform the method according to claim 11.

15. A signal processing apparatus (SP) comprising:
a memory configured to save a signal model; and
processor circuitry configured to cause to:
detect a signal after passage of radiation through a sample with an energy resolving detector;
measure a count rate for photonic interactions with the detector from the signal;
receive the measured count rate;
fit the signal model to the measured counts, wherein the signal model represents a conditional expectation of a frequency of at least uni-directional pulse crossing of at least one energy level, given a physical quantity of a material in a sample, wherein the fitting operation includes solving an objective function for a parameter for the physical quantity,
wherein a fidelity of the solved for parameter for the physical quantity is independent of a photon fluence of the radiation.

16. The apparatus according to claim 15, wherein the apparatus is configured to perform a method of processing a signal measured by a photon-counting detector after passage of radiation through a sample.

* * * * *